US012220154B2

(12) United States Patent
Qi et al.

(10) Patent No.: US 12,220,154 B2
(45) Date of Patent: Feb. 11, 2025

(54) MOTOR-DRIVEN FIXATOR TO APPLY MICROMOTION TO FRACTURE SITE TO ACCELERATE BONE HEALING

(71) Applicant: THE UNIVERSITY OF HONG KONG, Hong Kong (HK)

(72) Inventors: Weichen Qi, Hong Kong (HK); Xiaoreng Feng, Hong Kong (HK); Ka-Li Leung, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 277 days.

(21) Appl. No.: 17/784,731

(22) PCT Filed: Dec. 11, 2020

(86) PCT No.: PCT/CN2020/135629
§ 371 (c)(1),
(2) Date: Jun. 13, 2022

(87) PCT Pub. No.: WO2021/115418
PCT Pub. Date: Jun. 17, 2021

(65) Prior Publication Data
US 2023/0000524 A1   Jan. 5, 2023

Related U.S. Application Data

(60) Provisional application No. 62/947,569, filed on Dec. 13, 2019.

(51) Int. Cl.
*A61B 17/72* (2006.01)
*A61B 17/64* (2006.01)
(Continued)

(52) U.S. Cl.
CPC .......... *A61B 17/66* (2013.01); *A61B 17/6475* (2013.01); *A61B 2017/00017* (2013.01); *A61B 2017/564* (2013.01)

(58) Field of Classification Search
CPC ..... A61B 17/60; A61B 17/64; A61B 17/6491; A61B 17/66
See application file for complete search history.

(56) References Cited

U.S. PATENT DOCUMENTS 5,207,676 A * 5/1993 Canadell ............ A61B 17/6491
606/57
5,630,815 A * 5/1997 Pohl ...................... A61B 17/60
7/138
(Continued)

FOREIGN PATENT DOCUMENTS

CN   111345877 A * 6/2020 ............. A61B 17/62
DE   4035227 A1 * 2/1991 ............... A61H 1/00

OTHER PUBLICATIONS

International Search Report and Written Opinion for International Application No. PCT/CN2020/135629 mailed on Feb. 26, 2021, 14 pages.

*Primary Examiner* — Eduardo C Robert
*Assistant Examiner* — Michelle C Green
(74) *Attorney, Agent, or Firm* — Amin, Turocy & Watson, LLP

(57) ABSTRACT

Devices and methods for treating bone fractures involving a micromotional unit (6) that produces reciprocating displacement between two fracture fragments (1) to thereby apply controllable micromotion to a fracture site.

18 Claims, 6 Drawing Sheets

(51) Int. Cl.
  *A61B 17/66* (2006.01)
  *A61B 17/00* (2006.01)
  *A61B 17/56* (2006.01)

(56) References Cited

U.S. PATENT DOCUMENTS

| | | | |
|---|---|---|---|
| 2002/0010465 A1* | 1/2002 | Koo | A61B 17/62 606/57 |
| 2003/0149437 A1* | 8/2003 | Livne | A61L 27/222 606/76 |
| 2007/0173837 A1* | 7/2007 | Chan | A61B 17/66 606/63 |
| 2007/0225704 A1* | 9/2007 | Ziran | A61B 17/66 606/57 |
| 2019/0309839 A1 | 10/2019 | Zhao | |
| 2020/0197048 A1* | 6/2020 | Suddaby | A61B 17/7023 |

\* cited by examiner

MOTOR-DRIVEN FIXATOR TO APPLY MICROMOTION TO FRACTURE SITE TO ACCELERATE BONE HEALING

TECHNICAL FIELD

Disclosed are devices, systems, and methods that facilitate bone healing.

BACKGROUND

Fracture is the most common kind of bone disease, which usually requires expensive surgical treatment. According to the audit report issued by the International Osteoporosis Foundation (IOF) in 2013, high fracture rates with major increases in Asia is predicted by 2050 as the aging population, widespread vitamin D deficiency and low calcium intake.

Open reduction and implant fixation are considered as the standard treatment for fractures that are impossible to reduce manipulatively. A lot of implants have been developed and used widely in the fracture fixation, including dynamic compression plate (DCP), locking compression plate (LCP), intramedullary nail and external fixator. DCP, which provides absolute stability by achieving compression across the fracture line, can result in primary fracture healing without callus formation. LCP and intramedullary nail, however, provide relative stability that is good for secondly bone healing with massive bone callus formation. As the primary fracture healing requires longer time and has a higher re-fracture rate, the secondly bone healing induced by the relative stability is considered to be a better option for fracture fixation.

The relative stable implants can induce micromotion at the fracture site, which promotes callus formation and therefore accelerate the fracture healing. This theory has been proven by clinical observations and animal experiments. What is more, a series of micromotional implants have been designed to take advantage of this theory, such as the active plate, and dynamic locking screw. Even with good clinical results, the number of clinical reported fracture nonunion and delayed union with the relative stability fixation method is still high. It is reported that the overall rate of nonunion is up to 18.5% in the tibia diaphysis and the nonunion rate in the femoral shaft after reamed nailing is 1.7%. The effective range of strain that can promote fracture healing remains unclear. That could be the reason why the currently used relative stable implants showed inconsistent clinical results.

SUMMARY

The following presents a simplified summary of the disclosure in order to provide a basic understanding of some aspects of the disclosure. This summary is not an extensive overview of the disclosure. It is intended to neither identify key or critical elements of the disclosure nor delineate the scope of the disclosure. Rather, the sole purpose of this summary is to present some concepts of the disclosure in a simplified form as a prelude to the more detailed description that is presented hereinafter.

The subject disclosure provides devices, systems, and methods that involve micromotion with the appropriate model (including displacement range and frequency) that improves the callus formation along the fracture. A series of micromotional fixators accelerate fracture healing. Conventional 'dynamic fixators' rely on the bearing weight of the patient to produce the micromotion across the fracture line, which makes the micromotion uncontrollable. To produce controllable and accuracy micromotion at the fracture site, an electronic linear servo motor actuator and micromotional unit are designed to transform electric energy into reciprocating displacement between two fracture fragments. The electronic controller actuates micromotional unit to produce micromotion with per-set parameters and makes necessary compensation based on measured results of the displacement sensor. The micromotional unit can be removed after use. This orthopedic fixator can be used to treat fracture in various locations of patient in need thereof.

Essentially, a motor machine transforms electric energy into a reciprocating displacement between two components to apply controllable micromotion to the fracture site, which can be precisely adjusted by an electronic controller.

One aspect of the disclosure relates to external fixator for treating bone fractures, comprising a holder attached to bone at two locations, the two locations on opposite sides of a fracture site; a micromotional unit removably coupled to the holder, the micromotional unit configured to produce reciprocating displacement between two components to apply controllable micromotion to the fracture site; and a controller coupled to the micromotional unit, the controller for controlling the micromotional unit to produce reciprocating displacement.

The external fixator for treating bone fractures comprises: a holder attached to bone at two fracture fragments, the two fracture fragments respectively on opposite sides of a fracture site; a micromotional unit removably coupled to the holder, the micromotional unit configured to produce a reciprocating displacement between the two fracture fragments to apply a controllable micromotion to the fracture site; and a controller coupled to the micromotional unit, the controller configured for controlling the micromotional unit to produce the reciprocating displacement between the two fracture fragments.

Another aspect of the disclosure relates to method of treating bone fractures, involving attaching a holder attached to bone at two locations, the two locations on opposite sides of a fracture site; producing reciprocating displacement between two components a micromotional unit removably coupled to the holder thereby applying controllable micromotion to the fracture site; and controlling the reciprocating displacement to facilitate fracture healing at the fracture site.

The method of treating bone fractures comprises: attaching a holder to bone at two fracture fragments, the two fracture fragments respectively on opposite sides of a fracture site; producing reciprocating displacement between the two fracture fragments by a micromotional unit removably coupled to the holder, thereby applying a controllable micromotion to the fracture site; and controlling the reciprocating displacement between the two fracture fragments by a controller to facilitate fracture healing at the fracture site.

Still another aspect of the disclosure relates to a micromotional unit comprising: an outer tube, an inner tube, a motor, and a gear drive. At least a portion of the inner tube is inserted inside the outer tube; the motor and the gear drive are configured to transform an electrical signal into a relative axial displacement between the outer tube and the inner tube along an axial direction of the inner tube and the outer tube; and the outer tube and the inner tube are respectively connected with the two fracture fragments, so that the relative displacement between the outer tube and the inner tube produces the reciprocating displacement between the two fracture fragments.

To the accomplishment of the foregoing and related ends, the disclosure comprises the features hereinafter fully described and particularly pointed out in the claims. The following description and the annexed drawings set forth in detail certain illustrative aspects and implementations of the disclosure. These are indicative, however, of but a few of the various ways in which the principles of the disclosure may be employed. Other objects, advantages and novel features of the disclosure will become apparent from the following detailed description of the disclosure when considered in conjunction with the drawings.

DETAILED DESCRIPTION

With the ongoing investigation of bone healing mechanisms, the application of micromotion to a certain degree at the fracture site can accelerate fracture healing and reduce the incidence of nonunion. Consequently, a series of 'dynamic fixators', including external fixators and plates, have been designed to produce micromotion at the fracture site. All of the currently used 'dynamic fixators' rely on the bearing weight of the patient to produce the micromotion across the fracture line, which makes the micromotion uncontrollable. A problem is that improper micromotion parameters exert a negative impact on bone healing. For example, premature start or laggard end of micromotion application can delay the fracture repairing, and excessive displacement causes nonunion. Therefore, one significant limitation of currently used 'dynamic fixators' is the lack of feasible means to adjust the parameters of micromotion, such as range, frequency, duration and timing of micromotion, to produce proper micromotion to accelerate bone healing.

Figure 1:
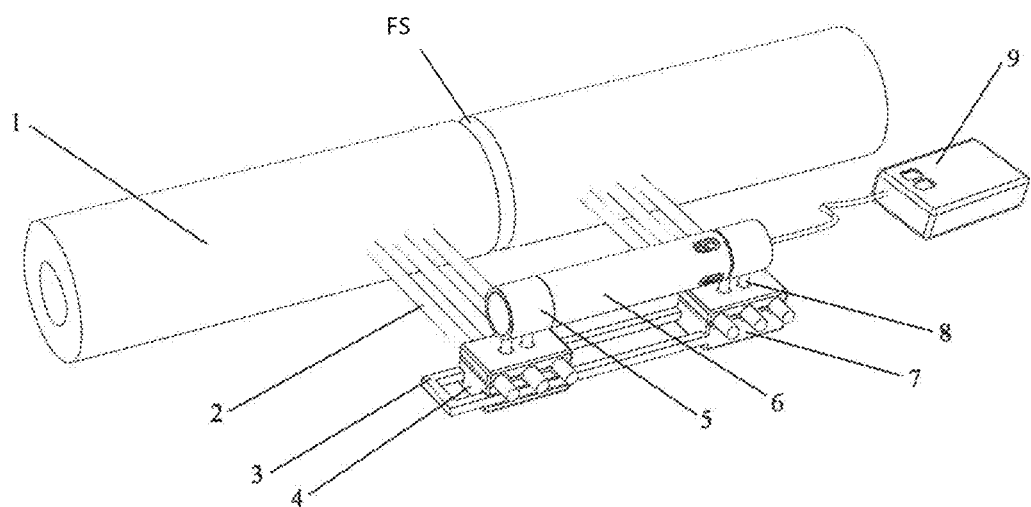
FIG. 1 depicts an external fixator in accordance with an embodiment showing 1—fracture fragment of patient; 2—K wire; 3—slideway on the main body of holder; 4—slide block; 5—adapter ring between micromotional unit and connecting rod; 6—micromotional unit; 7—main body of holder; 8—connecting rod; and 9—electronic controller.
Figure 2:
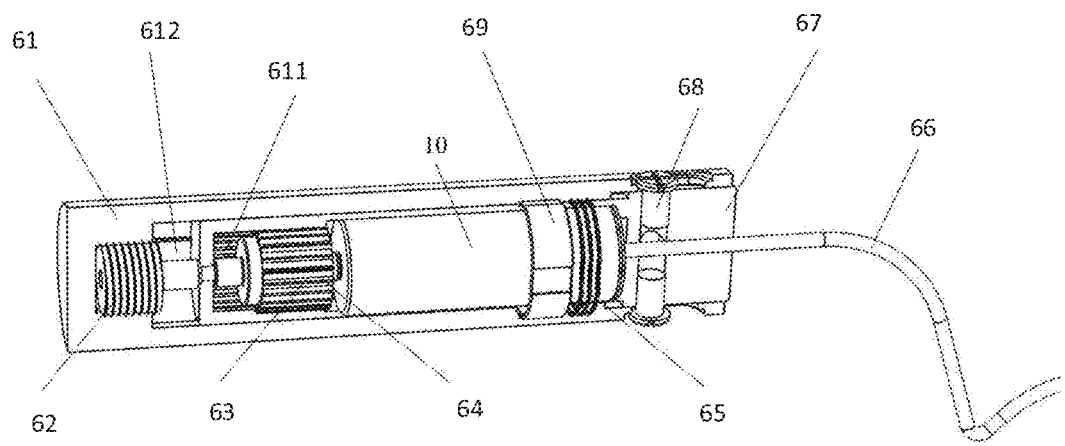
FIG. 2 depicts a structure of a micromotional unit in accordance with an embodiment showing 61—outer tube; 62—drive screw; 63—Elliptical gear; 64—strain wave generator; 65—sealing ring; 66—wire to electronic controller; 67—inner tube; 68—limiting screw; 69—displacement sensor; 610—motor; 611—circular ring gear; and 612—guide rail.
Figure 11:
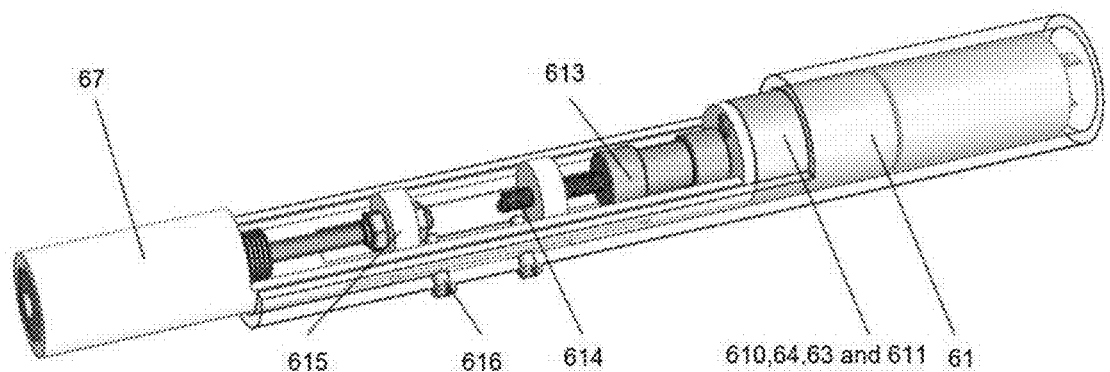
FIG. 11 shows a structure of a micromotional unit in accordance with an embodiment showing 613—coupling; 614—thread rod; 615—sliding block; 616—screw.

To produce controllable and proper micromotion for facilitating fracture healing, described herein is an external fixator. Referring to FIG. 1, FIG. 2 and FIG. 11, an electronic linear servo motor actuator 610 is designed to transform electric energy into reciprocating displacement between two fracture fragments 1. For example, a core component is a micromotional unit 6. For example, the micromotional unit 6 has four parts, an outer tube 61, an inner tube 67, a motor 610, and a gear drive. In terms of the working principle, for example, the motor 610 and the gear drive are configured to transform the electrical signal from an electronic controller 9 into the relative displacement between the outer tube 61 and the inner tube 67. For example, the outer tube 61 and the inner tube 67 are fixed at the proximal and distal fracture fragment respectively so that the reciprocating of the motor machine device 610 produces micromotion to patient's fracture site in a manner that facilitates and/or promotes fracture healing, especially compared to similar situations where the described external fixator is not employed.

As a product of orthopedic fixator to accelerate fracture healing, the advantages of the disclosure can be summarized at least in four keywords:

Autonomous—The external fixator can autonomously apply micromotion to patient's fracture site, instead of the relay on the patient's manual action or bearing weight, which makes the micromotion more effective than most conventional 'dynamic fixators'.

Programmable—The progress of the micromotional application, such as applied duration and timing, is programmable. According to the patient's healing status, the micromotional function can be turned on or off—that is, tailored to each circumstance.

Accuracy—The mechanical parameters, such as range and frequency, of each micromotional cycle are accurately controlled and compensated by a closed-loop controller based on a displacement sensor in micromotional unit.

Demountable—The micromotional unit of the external fixator is designed to be demountable at the end of each micromotional application to lighten the patient's burden.

This disclosure is about an external fixator to apply micromotion to patient's fracture site to improve bone healing. The external fixator comprises a micromotional unit 6, an electronic controller 9, and a holder. For example, two fracture fragments 1 of the patient are fixed on the main body 7 and slide block 4 of the holder respectively. For example, the main body 7 and slide block 4 are jointed with the inner tube 67 and the outer tube 61 of the micromotional unit 6 through two connective rods 8. For example, the micromotional unit 6 is configured to transfer the electric signal form the electronic controller 9 into circulatory displacement between the inner tube 67 and the outer tube 61. For example, a sensor 69 in the micromotional unit 6 is configured to measure the actual displacement and the electronic controller 9 is configured to make compensation based on this measured value. For example, the micromotional unit 6 is dismountable after use to release the patient's burden. This disclosure for example is used as an orthopedic fixator to treat fracture in various locations.

Referring to FIG. 1, an illustration in accordance with an embodiment is shown. The disclosure comprises a micromotional unit 6, an electronic controller 9, and a holder. For example, the micromotional unit 6 produces micromotion under the control of the electronic controller 9. For example, the holder is designed to provide stability to the patient's fracture site FS. For example, the main body 7 of the holder and the slide block 4 of the holder are fixed with the patient's proximal fragment and distal fracture fragment through three or so K wires 2 respectively. For example, the outer tube 61 and the inner tube 67 are inserted at the main body 7 of the holder and the slide block 4 of the holder through two or more connecting rods 8 respectively. For example, the micromotional unit is demountable, which is removed from holder after use.

FIG. 2 presents a drawing of the micromotional unit. For example, the micromotional unit comprises four parts, an outer tube 61, an inner tube 67, a motor 610, and a gear drive. For example, the motor 610 and the gear drive in the micromotional unit 6 are configured to transform the electrical signal from the electronic controller 9 into the relative displacement between the outer tube 61 and the inner tube 67. For example, a large-torque coreless motor 610 is rigidly fixed inside a purpose-designed space of the inner tube 67. The reasons for choosing coreless motor 610 as the prime mover are its advantages on high efficiency, quick response, tiny volume, and the like. For example, the coreless motor is a key technology to achieve an axial displacement of the micromotional unit 6. For example, an output shaft of the motor 610 is connected with a strain wave generator 64. For example, the strain wave generator 64 presses an elliptical gear 63 from its inside and forces the elliptical gear 63 mesh with a circular ring gear 611 in one end of the inner tube 67. For example, the strain wave generator 64, the elliptical gear 63, and the circular ring gear 611 constitute a harmonic gear drive to lower the rotational speed and increase the torque of the coreless motor 610. For example, the harmonic gear drive is an important component to complete the micromotion of the micromotional unit 6. For example, its characteristic on 'no backlash' is helpful to achieve the reciprocating motion of micromotional unit 6. For example, this drive can provide a high drive ratio (a ratio from 30:1 up to 300:1 is possible in the same space in which planetary gears typically only produce a 10:1 ratio) in a small volume, which saves precious space in the micromotional unit. For example, a drive screw 62 is coaxially connected with elliptical gear 63 through an output shaft, which converts the rotation into axial displacement. For example, a guide rail 612, such as four guide rails 612, provided between the inner tube 67 and outer tube 61 restrict the skewing or spin. For example, a limiting screw, such as four limiting screws, impose a restriction on the maximum displacement, though anywhere from two to 20 screws may be employed. For example, a sealing ring 65, such as three sealing rings, are set between the inner tube 67 and the outer tube 61 to keep the waterproof and sealing of the micromotional unit 6. For example, a displacement sensor 69, such as a magnetic grid, is placed in the sealing space as to export displacement signals to the closed-loop controller 9 through a wire 66, and the micromotion signal and the compensating signal from the controller 9 are transmitted to motor 610 through the same wire 66.

Figure 3:
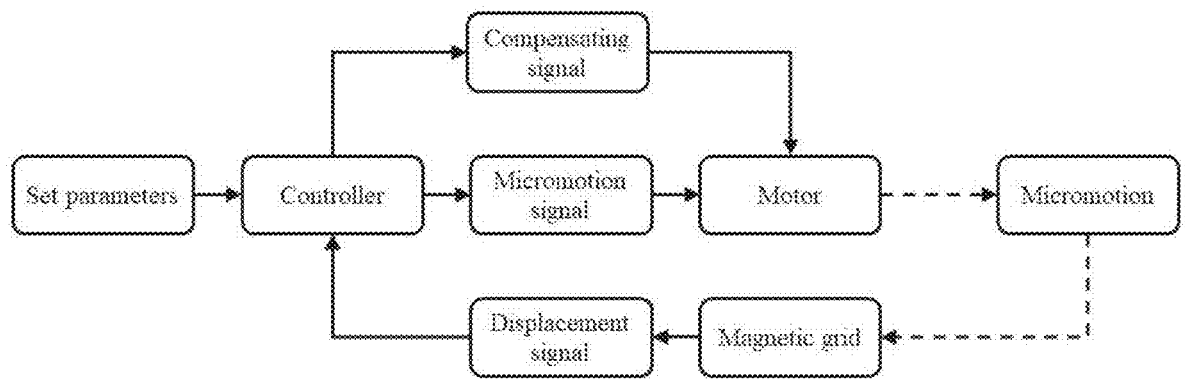
FIG. 3 illustrates a control logic diagram of an electronic controller in accordance with an embodiment.

For example, to facilitate the accurateness and controllability of the micromotional application, a closed-loop controller 9 to regulate the operation of the micromotional unit 6 is provided. For example, the controller 9 is a commercial SCM (single chip microcomputer) with I/O (input/output) model and PMW output (pulse width modulation) model. FIG. 3 shows an exemplary control logic diagram of the electronic controller 9, although others may be employed. For example, in the beginning, the user sets parameters of micromotion (such as range, frequency, duration, and timing), then the controller 9 produces a DC pulse signal (micromotion signal) to conduct the motor 610 in the micromotional unit 6 reciprocating motion. Meanwhile, the magnetic grid 69 detects the relative displacement of the micromotional unit 6, and then transform the displacement into a 'displacement signal'. For example, the controller 9 compares the received signal with user-entered parameters and adds an additional 'compensating signal' on the motor 610 to fix the error of displacement.

For example, a Micromotion Unit (MMU) 6 as described herein comprises components: a motor 610 such as a coreless motor; a gear drive such as a harmonic gear drive; and a displacement sensor such as a magnetic grid.

For example, to produce controllable and proper micromotion for fracture healing, inventors developed a motor-driven fixator. In this disclosure, for example, an electrical actuator such as a motor 610 is designed to transform electric energy into reciprocating displacement between two fracture fragments 1. For example, the core component is a micromotion unit (MMU) 6 which comprises four parts, an outer tube 61, an inner tube 67, a motor 610, and a gear drive. In terms of the working principle, for example, the motor 610 and the gear drive are configured to transform the electrical signal from an external controller 9 into the relative displacement between the outer tube 61 and the inner tube 67. For example, the outer tube 61 and the inner tube 67 are fixed at the proximal and distal fracture fragment respectively so that the reciprocating of motor machine device 610 produces micromotion to patient's fracture site FS.

For example, a large-torque coreless motor 610 is rigidly fixed inside a purpose-designed space of the inner tube 67. For example, the reasons for choosing coreless motor 610 as the prime mover are its advantages on high efficiency, quick response, tiny volume and the like. For example, the coreless motor 610 is a feature to facilitate achieving axial displacement of the MMU 6. For example, the output shaft of the motor 610 is connected with a strain wave generator 64.

For example, the strain wave generator 64 presses an elliptical gear 63 from its inside and forces the elliptical gear 63 mesh with a circular ring gear 611 in one end of inner tube 67. For example, the strain wave generator 64, the elliptical gear 63, and the circular ring gear 611 constitute a harmonic gear drive to lower the rotational speed and increase the torque of the coreless motor 610. For example, the harmonic gear drive is a notable component to complete the micromotion of the MMU 6—its characteristic of 'no backlash' is helpful to facilitate achieving the reciprocating motion of the MMU 6. For example, the drive provides a high drive ratio (a ratio from 30:1 up to 300:1 is possible in the same space) in a small volume. For example, the drive provides a high drive ratio (a ratio from 50:1 up to 250:1 in the same space) in a small volume. For example, a drive screw 62 is coaxially connected with elliptical gear 63 through an output shaft, which converts the rotation into axial displacement. For example, a guide rail 612, such as four guide rails 612, provided between the inner tube 67 and the outer tube 61 restrict the skewing or spin. For example, a limiting screw 68, such as four limiting screws 68, impose a restriction on the maximum displacement. For example, a sealing ring 65, such as three sealing rings 65, are set between the inner tube 67 and the outer tube 61 to keep the waterproof and sealing of MMU 6.

For example, a displacement sensor 69, such as the magnetic grid, is placed in the sealing space to export displacement signals to the closed-loop controller 9 through a wire 66, and the micromotion signal and the compensating signal from the controller 9 are transmitted to motor 610 through the same wire 610.

Figure 4:
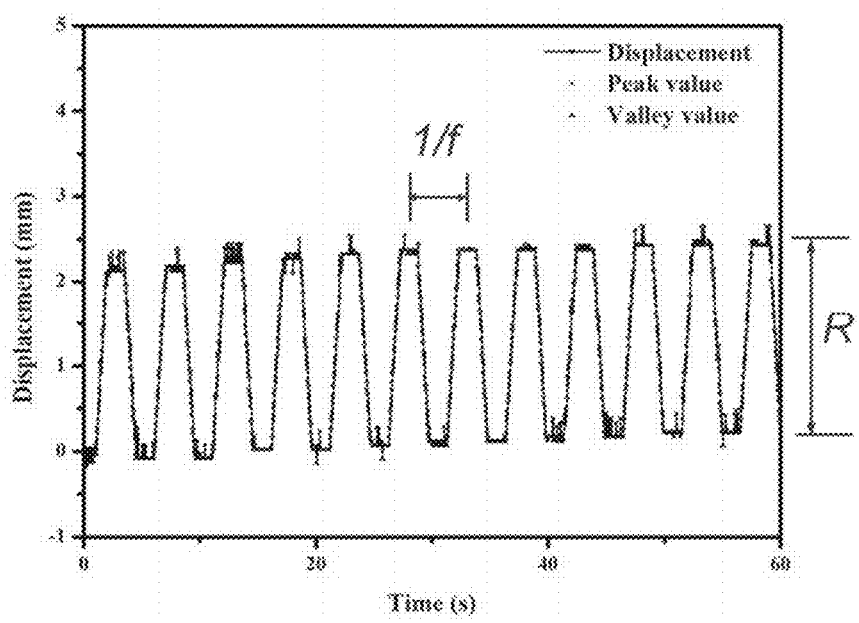
FIG. 4 shows a measured displacement-time curve of a micromotional unit in accordance with an embodiment.

FIG. 4 illustrates the measured displacement-time curve of the micromotional unit; that is, calculation of frequency (f) and range (R) using an MMU in accordance with the description herein. For example, the micromotional unit 6 was set to produce micromotion at the range of 2 mm in the frequency of 0.2 Hz. The displacement-time curve proves the compensation function has been realized by the electronic controller.

Figure 5:
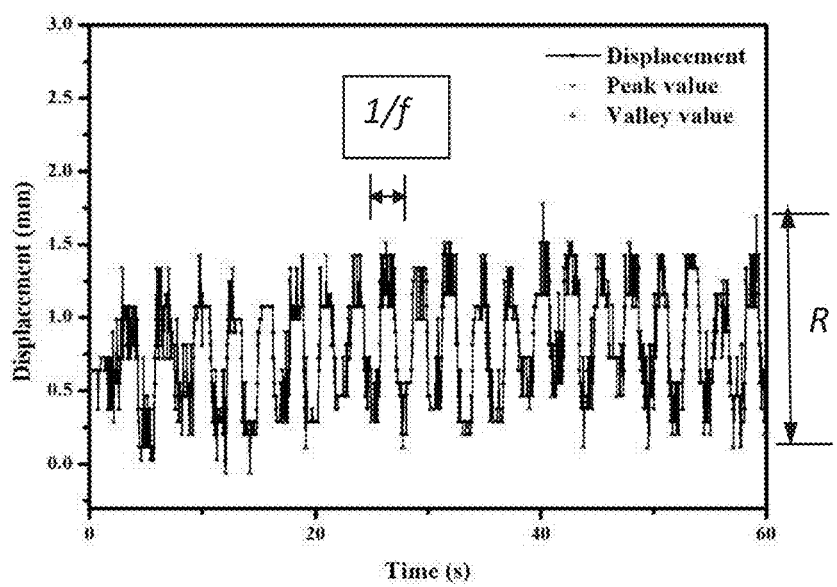
FIG. 5 shows a measured displacement-time curve of a conventional micromotional unit.

FIG. 5 illustrates the measured displacement-time curve of a conventional device; that is, calculation of frequency (f) and range (R) using the Orthofix® external fixator.

Figure 6:
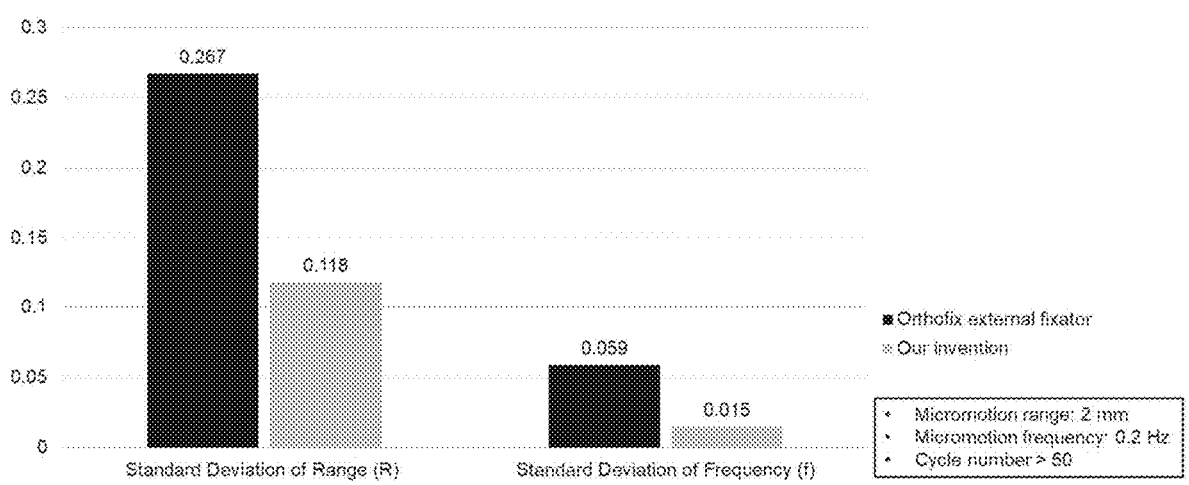
FIG. 6 shows a comparison between an external fixator in accordance with an embodiment and the conventional Orthofix® external fixator on micromotion accuracy.

FIG. 6 lists a comparison between an MMU/an external fixator in accordance with an embodiment and a commercially available Orthofix® external fixator on micromotion accuracy. The external fixator in accordance with this disclosure shows a significant advantage in the accuracy of micromotional range and micromotional frequency compared to the commercially available Orthofix® external fixator. As demonstrated in FIG. 6, the MMU in accordance with an embodiment can provide a more uniform and stable micromotion than the Orthofix's product (with a smaller standard deviation in both range (R) and frequency (f)).

Figure 7:
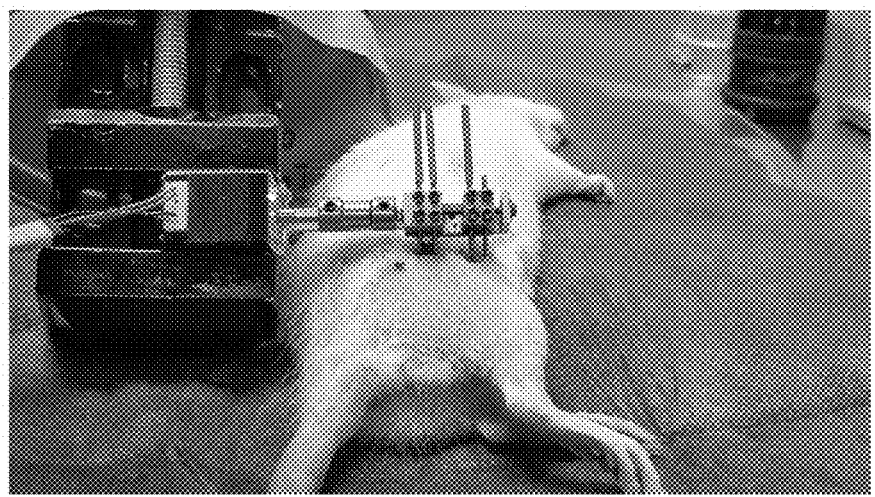
FIG. 7 shows application of a micromotional unit (MMU) on fracture site in accordance with an embodiment.

FIG. 7 shows application of MMU on fracture site FS after two week's postoperative recovery. Although not specifically tied to FIG. 7, an exemplary range for the application is 0.246±0.020 mm and an exemplary frequency is 0.644±0.032 Hz.

Figure 8:
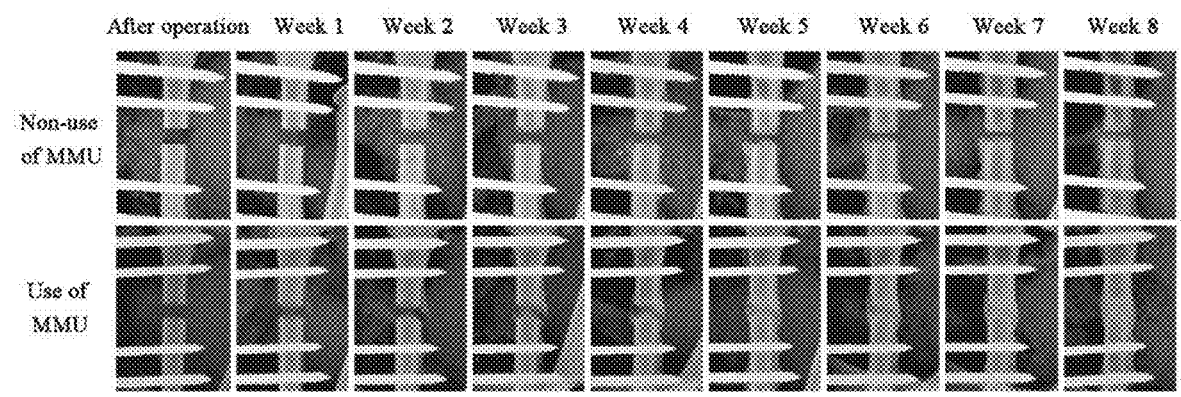
FIG. 8 depicts X-ray images showing use and non-use of an MMU on fracture site in accordance with an embodiment.

FIG. 8 depicts X-ray images of a control group without using an MMU and the micromotion group using MMU in accordance with this disclosure.

Figure 9:
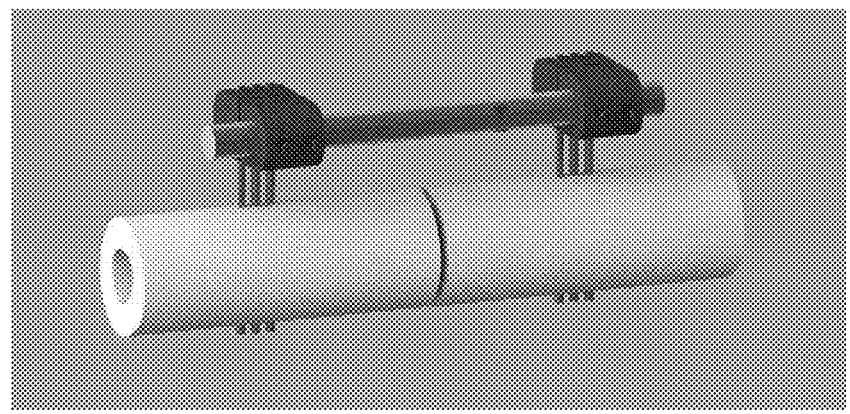
FIG. 9 shows an external fixator with MMU in accordance with an embodiment.

For example, there are numerous applications of the MMU 6 in accordance with this disclosure. The MMU 6 is the core component, which produces reciprocating displacement alone its axial direction. For example, the closed-loop controller 9 supplies power to the MMU 6 and controls the MMU 6 via the changing of the electrical signal. As shown in FIG. 9, the MMU for example is configured as one of various forms of orthopedic fixators to satisfy different requirements of fracture classifications on fixation, for example, for fracture reduction, limb lengthening and scoliosis correction. For example, FIG. 9 shows a micromotional external fixator.

Figure 10:
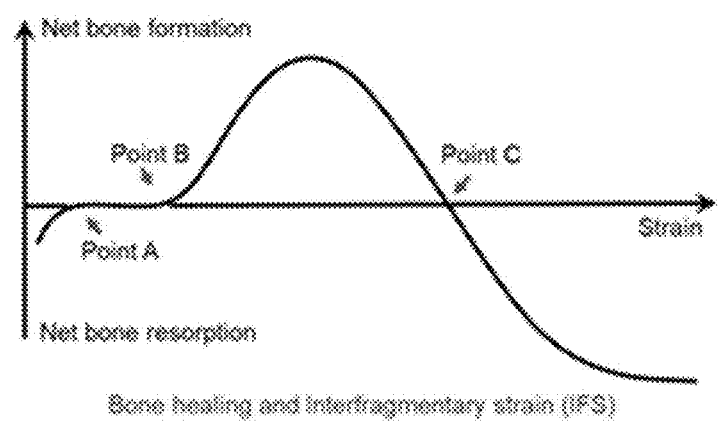
FIG. 10 shows the relationship between bone formation and interfragmentary strain (IFS).

Having regular frequencies and ranges of micromotion is important in clinical treatment. It has been noticed that the micromotion within a certain range can promote bone healing, however, below or above this optimal range can lead to the delayed union or the nonunion. FIG. 10 shows the relationship between bone formation and interfragmentary strain (IFS). If the IFS higher than Point C or lower than Point A, the delayed union or the nonunion would happen. According to current bone healing theory, the optimal range of micromotion makes IFS remain between Point A and Point C in FIG. 10, the bone healing theoretically is enhanced by the improvement of callus formation along with the fracture site FS. And the rate of delayed union and non-union is decreased. As a result, irregular micromotion may cause invalid stimulate even brings a negative effect to fracture healing.

Meanwhile, the Ortohfix® fixator can only limit the maximum displacement by a stop block. However, in some extreme cases, the delayed union and the non-union still occur since interfragmentary strain is too low.

For example, the external fixator described herein is designed to solve this problem by monitoring the actual range and frequency and make necessary compensation. And the micromotional range can be accuracy controlled in the optimal range, which is a significant advance in the art.

For example, the external fixator described herein operates in a range with a frequency that facilitates fracture healing with a relatively low standard deviation. For example, the external fixator operates in a range from 0.01 mm to 5 mm. For example, the external fixator operates in a range from 0.1 mm to 3 mm. For example, the external fixator operates in a given range with a standard deviation from ±0.001 mm to 0.1 mm. For example, the external fixator operates in a given range with a standard deviation from ±0.01 mm to 0.075 mm. For example, the external fixator operates at a frequency from 0.05 Hz to 5 Hz. For example, the external fixator operates at a frequency from 0.1 Hz to 2.5 Hz. For example, the external fixator operates at a given frequency with a standard deviation from 0.001 Hz to 0.1 Hz. For example, the external fixator operates at a given frequency with a standard deviation from 0.01 Hz to 0.05 Hz.

For example, the external fixator described herein can provide real-time feedback to surgeons and help them timely adjust the micromotional parameters. It is an important therapeutic reference to surgeons because both exaggerate micromotion and inadequate micromotion cause detrimentally the delayed union or the nonunion.

For example, the electric controller 9 described herein reduces the workload of patents. For example, according to the Orthofix®'s protocol, the patient should shake a handle on one side of fixator for 10 minutes daily, and produce cycle micromotion for 2-3 weeks, then the patient should produce progressive loading for 2-3 weeks more by the same method. These complicated operations and repetitive work are advantageously executed by the electric controller 9 as described herein, which highly shortens the learning curve.

For example, the external fixator described herein shows significant advantages on the integrated design, the modular construction and the compatibility compared with current commercial fixator. For example, the integrated design enables all movable parts of the micromotional unit to be packaged into one tubular shell. This integrated design minimizes the risk of failure due to foreign matter (such as water, ash, and fiber) entering the mechanical part and brings great benefit to the reliability of micromotional fixator.

For example, the modular construction enables the connections among the micromotional unit 6, the electronic controller 9, and the holder to be dismountable. For example, the micromotional unit 6 and the electronic controller 9 are removed from the holder at the end of each micromotional application to lighten the patient's burden.

For example, the external fixator described herein has compatibility with a commercial fixator in that the connector on the micromotional unit 6 is designed to be compatible with the commercial fixator. For example, the micromotional unit can take place of the manual adaptor on Orthofix®'s product to furnish it with the ability of autonomous working.

According to our results on rat model, a 20% strain of micromotional range showed the most significant improvement on fracture healing, but strains from 2% to 40% can be employed. For example, strains from 15% to 25% are employed. For example, strains from 10% to 20% are employed.

For example, the displacement sensor 69 and the electric controller 9 make the MMU 6 controllable. Also, the harmonic gear drive facilitates the characteristic on 'no backlash' to achieve the reciprocating motion of MMU 6.

For example, the MMU needs reciprocating motion in a high speed, and the mechanical parts make quick response to the signal form the electronic controller 9. For example, the selection of motor 610 and gear drive fulfills this requirement. For example, for the cordless motor 610, the rotating part on this kind of motor 610 is lighter than step motor and other common motor. For example, this motor achieves the action of 'rotation-stop-reverse rotation' in a high speed. For example, the step motor is more likely to achieve a high accuracy action. And the extremely high transmission ratio of harmonic gear drive undercuts the advantage of step motor in accuracy.

With respect to any figure or numerical range for a given characteristic, a figure or a parameter from one range may be combined with another figure or a parameter from a different range for the same characteristic to generate a numerical range.

For example, an external fixator for treating bone fractures is provided. For example, referring to FIG. 1, the external fixator comprises: a holder attached to bone at two fracture fragments 1, the two fracture fragments 1 respectively on opposite sides of a fracture site FS; a micromotional unit 6 removably coupled to the holder, the micromotional unit 6 configured to produce a reciprocating displacement between the two fracture fragments 1 to apply a controllable micromotion to the fracture site FS; and a controller 9 coupled to the micromotional unit 6, the controller 9 configured for controlling the micromotional unit 6 to produce the reciprocating displacement between the two fracture fragments 1.

For example, referring to FIG. 2, the micromotional unit 6 comprises an outer tube 61, an inner tube 67, a motor 610, and a gear drive, and at least a portion of the inner tube 67 is inserted inside the outer tube 61; the motor 610 and the gear drive are configured to transform an electrical signal from the controller 9 into a relative axial displacement between the outer tube 61 and the inner tube 67 along an axial direction of the inner tube 67 and the outer tube 61; and the outer tube 61 and the inner tube 67 are respectively connected with the two fracture fragments 1, so that the relative axial displacement between the outer tube 61 and the inner tube 67 produces the reciprocating displacement between the two fracture fragments 1.

For example, referring to FIG. 2, the gear drive is a harmonic gear drive, and the harmonic gear drive comprises a strain wave generator 64, an elliptical gear 63, and a circular ring gear 611; and the strain wave generator 64 is connected with an output shaft of the motor 610, the circular ring gear 611 is provided on the inner tube 67, and the motor 610 drives the strain wave generator 64 to press the elliptical gear 63 from an inside of the elliptical gear 63 to force the elliptical gear 63 mesh with the circular ring gear 611.

For example, referring to FIG. 2, the micromotional unit 6 further comprises a drive screw 62 coaxially connected with elliptical gear 63 and meshed with the outer tube 61, and the motor 610 drives the drive screw 62 to rotate at the same time the motor 610 drives the strain wave generator 64 to press the elliptical gear 63 from the inside of the elliptical gear 63, so as to produce the relative axial displacement between the outer tube 61 and the inner tube 67.

For example, the motor 610 rotates in a first direction, the outer tube 61 and the inner tube 67 move towards each other along the axial direction of the inner tube 67 and the outer tube 61; and the motor 610 rotates in a second direction opposite to the first direction, the outer tube 61 and the inner tube 67 move away from each other along the axial direction of the inner tube 67 and the outer tube 61.

For example, FIG. 11 shows a structure of a micromotional unit in accordance with an embodiment, in which the motor 610, the strain wave generator 64, the elliptical gear 63, and the circular ring gear 611 are integrated together as a block for simplicity, details thereof and connections therebetween may refer to FIG. 2. To show the internal structure, parts of the outer tube 61 and inner tube 67 have been removed in the FIG. 11. For example, referring to FIG. 11, the micromotional unit 6 further comprises a threaded rod 614 connected to the motor 610, and a sliding block 615 connected to the threaded rod 613; and the motor 610 drives the sliding block 615 to move at the same time the motor 610 drives the strain wave generator 64 to press the elliptical gear 63 from the inside of the elliptical gear 63, the outer tube 61 is connected with the sliding block 615 and moves with the sliding block 615, so as to produce the relative axial displacement between the outer tube 61 and the inner tube 67. For example, the threaded rod 614 is connected to the motor 610 by a coupling 613. For example, the outer tube 61 is connected with the sliding block 615 by a screw 616. It should be noted that, the micromotional unit 6 also comprise the displacement sensor 69, details thereof may refer to FIG. 2. For example, the sliding block 615 is connected to the displacement sensor 69.

For example, referring to FIG. 2, the micromotional unit 6 further comprises a displacement sensor 69 detecting the relative axial displacement between the inner tube 67 and the outer tube 61, transforming the relative axial displacement into a displacement signal, and exporting the displacement signal to the controller 9. Then, based on the displacement signal, the controller 9 determines whether a compensating signal for compensating the electrical signal from the controller. In this way, the external fixator described herein is designed to monitor the actual micromotion applied to the fracture site and make necessary compensation. And the micromotion applied to the fracture site can be accuracy controlled in the optimal range, which is a significant advance in the art. For example, the compensating signal comprises: whether the electrical signal from the controller is necessary to be compensated or not; and if necessary, how much the compensation amount is. For example, the displacement sensor 69 is a magnetic grid.

For example, the motor 610 is a coreless motor. For example, the coreless motor 610 is rigidly fixed inside a purpose-designed space of the inner tube 67.

For example, referring to FIG. 2, the micromotional unit 6 further comprises a guide rail 612 provided between the inner tube 67 and outer tube 61 and extending along the axial direction of the inner tube 67 and the outer tube 61, so as to restrict skewing or spin between the outer tube 61 and the inner tube 67.

For example, referring to FIG. 2, the micromotional unit 6 further comprises a limiting screw 68 imposing a restriction on a maximum relative displacement between the outer tube 61 and the inner tube 67.

For example, referring to FIG. 2, the micromotional unit 6 further comprises a sealing ring 65 provided between the inner tube 67 and the outer tube 61.

For example, referring to FIG. 1, the holder comprises a main body 7 and a movable block 4, the movable block 4 is movable with respect to the main body 7, and the main body 7 and the movable block 4 are respectively attached to the two fracture fragments 1; the outer tube 61 and the inner tube 67 are respectively connected with the main body 7 and the movable block 4 of the holder; and the relative axial displacement between the outer tube 61 and the inner tube 67 produces a reciprocating displacement between the main body 7 and the movable block 4 of the holder, so as to produce the reciprocating displacement between the two fracture fragments 1. For example, during the micromotion is applied to the fracture site FS, the movable block 4 is movable with respect to the main body 7; during the micromotion is not applied to the fracture site FS, the movable block 4 is locked and is not movable with respect to the main body 7.

For example, referring to FIG. 1, the holder further comprises a slideway 3 connected with the main body 7, the movable block 4 is a slide block slidable on the slideway 3 with respect to the main body 7.

For example, the holder comprises a main body 7 and two movable blocks 4, each of the two movable blocks 4 is movable with respect to the main body 7, and the two movable blocks 4 are respectively attached to the two fracture fragments 1; the outer tube 61 and the inner tube 67 are respectively connected with the two movable blocks 4 of the holder; and the relative axial displacement between the outer tube 61 and the inner tube 67 produces a reciprocating displacement between the two movable blocks 4 of the holder, so as to produce the reciprocating displacement between the two fracture fragments 1. For example, during the micromotion is applied to the fracture site FS, the two movable blocks 4 are movable with respect to the main body 7; during the micromotion is not applied to the fracture site FS, the two movable blocks 4 are locked and are not movable with respect to the main body 7.

For example, the holder further comprises a slideway 3 connected with the main body 7, each of the two movable blocks 4 is a slide block slidable on the slideway 3 with respect to the main body 7.

For example, a method of treating bone fractures is provided, comprising: attaching a holder to bone at two fracture fragments 1, the two fracture fragments 1 respectively on opposite sides of a fracture site FS; producing reciprocating displacement between the two fracture fragments 1 by a micromotional unit 6 removably coupled to the holder, thereby applying a controllable micromotion to the fracture site FS; and controlling the reciprocating displacement between the two fracture fragments 1 by a controller 9 to facilitate fracture healing at the fracture site.

For example, the method further comprising: removing the micromotional unit 6 from the holder at an end of applying the controllable micromotion to the fracture site FS to lighten the patient's burden.

For example, the micromotional unit comprises an outer tube 61, an inner tube 67, a motor 610, and a gear drive, and at least a portion of the inner tube 67 is inserted inside the outer tube 61; the motor 610 and the gear drive are configured to transform an electrical signal from the controller 9 into a relative axial displacement between the outer tube 61 and the inner tube 67 along an axial direction of the inner tube 67 and the outer tube 61; the relative axial displacement between the outer tube 67 and the inner tube 61 produces the reciprocating displacement between the two fracture fragments 1; and the method further comprises: detecting the relative axial displacement between the inner tube 67 and the outer tube 61, transforming the relative axial displacement into a displacement signal, and exporting the displacement signal to the controller 9; and determining a compensating signal for compensating the electrical signal from the controller 9 based on the displacement signal. In this way, the external fixator described herein is designed to monitor the actual micromotion applied to the fracture site and make necessary compensation. And the micromotion applied to the fracture site can be accuracy controlled in the optimal range, which is a significant advance in the art. For example, the compensating signal comprises: whether the electrical signal from the controller is necessary to be compensated or not; and if necessary, how much the compensation amount is. For example, the displacement sensor 69 is a magnetic grid.

For example, the two fracture fragments 1 are spaced from each other by a distance at the fracture site FS; and the method further comprises: producing the displacement between the two fracture fragments 1 to be 10%-20%, preferably 20%, of the distance. That is, strains from 10% to 20% are employed, preferably, strain of 20% is employed.

For example, strains from 2% to 40% may be employed. For example, strains from 15% to 25% may be employed.

For example, the method further comprises: producing reciprocating displacement in a range with a frequency that facilitates fracture healing at the fracture site with a relatively low standard deviation.

For example, a micromotional unit 6 is provided, comprising: an outer tube 61, an inner tube 67, a motor 610, and a gear drive; at least a portion of the inner tube 67 is inserted inside the outer tube 61; the motor 610 and the gear drive are configured to transform an electrical signal into a relative axial displacement between the outer tube 61 and the inner tube 67 along an axial direction of the inner tube 61 and the outer tube 67; and the outer tube 61 and the inner tube 67 are respectively connected with two fracture fragments 1, so that the relative axial displacement between the outer tube 61 and the inner tube 67 produces a reciprocating displacement between the two fracture fragments 1.

For example, the micromotional unit produces reciprocating displacement in a range with a frequency that facilitates fracture healing at the fracture site with a relatively low standard deviation.

Figure 12:
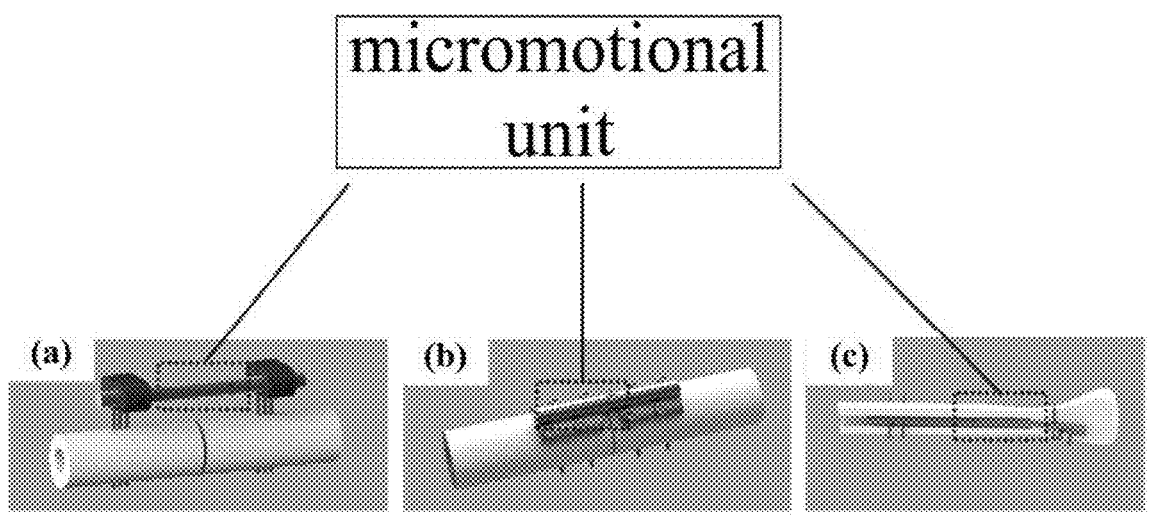
FIG. 12 shows various applications of an MMU in accordance with an embodiment.

For example, the micromotional unit 6 has numerous potential applications. For example, referring to FIG. 12, the micromotional unit 6 is applied to: (a) a micromotional external fixator; (b) a micromotional plate; and (c) a micromotional intramedullary nail. It should be noted that, the applications of the micromotional unit 6 are not limited to cases illustrated in FIG. 12.

Other than in the operating examples, if any, or where otherwise indicated, all numbers, values and/or expressions referring to parameters, measurements, conditions, etc., used in the specification and claims are to be understood as modified in all instances by the term "about."

While the disclosure is explained in relation to certain embodiments, it is to be understood that various modifications thereof will become apparent to those skilled in the art upon reading the specification. Therefore, it is to be understood that the disclosure disclosed herein is intended to cover such modifications as fall within the scope of the appended claims.

Further descriptions are included in Appendix 1.

What is claimed is:

1. An external fixator for treating bone fractures, the external fixator comprising:
   a holder attached to bone at two fracture fragments, the two fracture fragments respectively on opposite sides of a fracture site;
   a micromotional unit removably coupled to the holder, the micromotional unit configured to produce a reciprocating displacement between the two fracture fragments to apply a controllable micromotion to the fracture site; and
   a controller coupled to the micromotional unit, the controller configured for controlling the micromotional unit to produce the reciprocating displacement between the two fracture fragments, wherein the micromotional unit comprises an outer tube, an inner tube, a motor, and a gear drive, and at least a portion of the inner tube is inserted inside the outer tube, wherein the motor and the gear drive are configured to transform an electrical signal from the controller into a relative axial displacement between the outer tube and the inner tube along an axial direction of the inner tube and the outer tube, wherein the outer tube and the inner tube are respectively connected with the two fracture fragments, so that the relative axial displacement between the outer tube and the inner tube produces the reciprocating displacement between the two fracture fragments, wherein the gear drive is a harmonic gear drive, and the harmonic gear drive comprises a strain wave generator, an elliptical gear, and a circular ring gear; and wherein the strain wave generator is connected with an output shaft of the motor, the circular ring gear is provided on the inner tube, and the motor drives the strain wave generator to press the elliptical gear from an inside of the elliptical gear to force the elliptical gear mesh with the circular ring gear.

2. The external fixator according to claim 1, wherein the micromotional unit further comprises a drive screw coaxially connected with elliptical gear and meshed with the outer tube, and the motor drives the drive screw to rotate at the same time the motor drives the strain wave generator to press the elliptical gear from the inside of the elliptical gear, so as to produce the relative axial displacement between the outer tube and the inner tube.

3. The external fixator according to claim 1, wherein the micromotional unit further comprises a threaded rod connected to the motor, and a sliding block connected to the threaded rod; and the motor drives the sliding block to move at the same time the motor drives the strain wave generator to press the elliptical gear from the inside of the elliptical gear, the outer tube is connected with the sliding block and moves with the sliding block, so as to produce the relative axial displacement between the outer tube and the inner tube.

4. The external fixator according to claim 1, wherein the micromotional unit further comprises a displacement sensor detecting the relative axial displacement between the inner tube and the outer tube, transforming the relative axial displacement into a displacement signal, and exporting the displacement signal to the controller.

5. The external fixator according to claim 4, wherein the displacement sensor comprises a magnetic grid.

6. The external fixator according to claim 1, wherein the motor is a coreless motor.

7. The external fixator according to claim 1, wherein the micromotional unit further comprises a guide rail provided between the inner tube and outer tube and extending along the axial direction of the inner tube and the outer tube, so as to restrict skewing or spin between the outer tube and the inner tube.

8. The external fixator according to claim 1, wherein the micromotional unit further comprises a limiting screw imposing a restriction on a maximum relative displacement between the outer tube and the inner tube.

9. The external fixator according to claim 1, wherein the micromotional unit further comprises a sealing ring provided between the inner tube and the outer tube.

10. The external fixator according to claim 1, wherein the holder comprises a main body and a movable block, the movable block is movable with respect to the main body, and the main body and the movable block are respectively attached to the two fracture fragments;

the outer tube and the inner tube are respectively connected with the main body and the movable block of the holder; and the relative axial displacement between the outer tube and the inner tube produces a reciprocating displacement between the main body and the movable block of the holder, so as to produce the reciprocating displacement between the two fracture fragments.

11. The external fixator according to claim 10, wherein the holder further comprises a slideway connected with the main body, the movable block is a slide block slidable on the slideway with respect to the main body.

12. The external fixator according to claim 1, wherein the holder comprises a main body and two movable blocks, each of the two movable blocks is movable with respect to the main body, and the two movable blocks are respectively attached to the two fracture fragments;

the outer tube and the inner tube are respectively connected with the two movable blocks of the holder; and the relative axial displacement between the outer tube and the inner tube produces a reciprocating displacement between the two movable blocks of the holder, so as to produce the reciprocating displacement between the two fracture fragments.

13. The external fixator according to claim 12, wherein the holder further comprises a slideway connected with the main body, each of the two movable blocks is a slide block slidable on the slideway with respect to the main body.

14. A method of treating bone fractures, comprising:

attaching a holder to bone at two fracture fragments, the two fracture fragments respectively on opposite sides of a fracture site;

producing reciprocating displacement between the two fracture fragments by a micromotional unit removably coupled to the holder, thereby applying a controllable micromotion to the fracture site; and controlling the reciprocating displacement between the two fracture fragments by a controller to facilitate fracture healing at the fracture site, wherein the micromotional unit comprises an outer tube, an inner tube, a motor, and a gear drive, and at least a portion of the inner tube is inserted inside the outer tube, wherein the motor and the gear drive are configured to transform an electrical signal from the controller into a relative axial displacement between the outer tube and the inner tube along an axial direction of the inner tube and the outer tube, wherein the outer tube and the inner tube are respectively connected with the two fracture fragments, so that the relative axial displacement between the outer tube and the inner tube produces the reciprocating displacement between the two fracture fragments, and wherein the micromotional unit further comprises a guide rail provided between the inner tube and outer tube and extending along the axial direction of the inner tube and the outer tube, so as to restrict skewing or spin between the outer tube and the inner tube.

15. The method according to claim 14, further comprising:

removing the micromotional unit from the holder at an end of applying the controllable micromotion to the fracture site.

16. The method according to claim 14, wherein the method further comprises:
detecting the relative axial displacement between the inner tube and the outer tube, transforming the relative axial displacement into a displacement signal, and exporting the displacement signal to the controller; and
determining a compensating signal for compensating the electrical signal from the controller based on the displacement signal.

17. The method according to claim 14, wherein the two fracture fragments are spaced from each other by a distance at the fracture site; and
the method further comprises: producing the displacement between the two fracture fragments to be 10%-20% of the distance.

18. A micromotional unit comprising: an outer tube, an inner tube, a motor, and a gear drive, wherein
at least a portion of the inner tube is inserted inside the outer tube;
the motor and the gear drive are configured to transform an electrical signal from the controller into a relative axial displacement between the outer tube and the inner tube along an axial direction of the inner tube and the outer tube; and
the outer tube and the inner tube are respectively connected with two fracture fragments, so that the relative axial displacement between the outer tube and the inner tube produces a reciprocating displacement between the two fracture fragments,
wherein the holder comprises a main body and a movable block, the movable block is movable with respect to the main body, and the main body and the movable block are respectively attached to the two fracture fragments,
wherein the outer tube and the inner tube are respectively connected with the main body and the movable block of the holder, and
wherein the relative axial displacement between the outer tube and the inner tube produces a reciprocating displacement between the main body and the movable block of the holder, so as to produce the reciprocating displacement between the two fracture fragments.

\* \* \* \* \*